United States Patent [19]

Zaiger

[11] Plant 4,108

[45] Sept. 20, 1977

[54] PEACH TREE

[76] Inventor: Chris Floyd Zaiger, 537 Rosemore Ave., Modesto, Calif. 95351

[21] Appl. No.: 709,615

[22] Filed: July 28, 1976

[51] Int. Cl.[2] ..... A01H 5/03

[52] U.S. Cl. ..... Plt./41

[58] Field of Search ..... Plt./43

*Primary Examiner*—Robert E. Bagwill

[57] ABSTRACT

A variety of peach tree which is of large size, vigorous upright growth and the tree being a productive and regular bearer of large, early ripening, clingstone fruit having firm, yellow flesh, and a high degree of red skin color.

1 Drawing Figure

ORIGIN OF THE VARIETY

My new variety of peach tree was originated by me in my experimental orchard near Modesto, Calif., as an open pollenated seedling of Royal Gold Peach (U.S. Plant Pat. No. 2,663).

ASEXUAL REPRODUCTION OF THE VARIETY

Asexual reproduction of the new variety by budding as performed at Modesto, Calif., shows that said characteristics come true to form and are established and transmitted through succeeding propagations.

SUMMARY OF THE VARIETY

My present discovery relates to a new and distinct variety of peach tree. Its novelty consists of the following unique combination of features which are outstanding in the new variety:

1. A high degree of desirable red skin color;
2. The large size of the fruit;
3. The firmness of the fruit and its good shipping characteristics;
4. Coloring of the fruit two to three weeks before ripening;
5. The early ripening of the fruit occurring in late May. In comparison to the seed parent, my new variety is larger in size, has a greater distribution of uniform fruit throughout the tree and has a higher degree of red skin color, the ripening date being essentially the same.

DESCRIPTION OF THE PHOTOGRAPH

The accompanying photographs show typical specimens of the foliage and fruit of my new variety with upper and lower surfaces of the foliage being illustrated and exterior and a sectional view of the fruit being shown. These illustrations were taken shortly after being picked at maturity (shipping ripe). The colors are as nearly true as is reasonably possible in a color representation of this type.

DESCRIPTION OF THE VARIETY

The following is a detailed description of the foliage and fruit of my new variety, as based upon observations of specimens grown at Modesto, Calif., with color terminology in accordance with Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Bearing.*—Regular.

Trunk:
- *Size.*—Medium to stocky.

- *Surface.*—Medium to shaggy.

Branches:
- *Size.*—Medium to stocky.
- *Surface.*—Medium shaggy.

Leaves:
- *Size.*—Average length — 7 inches. Average width — $1\frac{3}{4}$ inches.
- *Margin.*—Crenate.
- *Petiole.*—Medium length.
- *Glands.*—Reniform.
- *Color.*—Upper surface — deep green (28E7) to (28E8). Lower surface — spinach green (29D5) to (29D6).

Flower buds:
- *Size.*—Large.
- *Length.*—Medium.

Flowers:
- *Size.*—Large, showy.
- *Color.*—Pink.
- *Pollen.*—Present.
- *Blooming period.*—Feb. 27, 1976 to Mar. 13, 1976.

Fruit:
- *Maturity when described.*—Hard ripe.
- *Date of first picking.*—May 22, 1976.
- *Date of last picking.*—May 28, 1976.
- *Size.*—Large; Diameter axially — $2\frac{1}{2}''$ to $3\frac{1}{8}''$; Suture plane — 2 5/16" to 3".
- *Form.*—Uniform; Symmetrical; Globose.
- *Suture.*—Shallow and nearly disappears at maturity.
- *Ventral surface.*—Rounded and only very slightly lipped.
- *Apex.*—Short.
- *Cavity.*—Rounded; Average depth — $\frac{1}{8}''$; Average breadth — 1".

Flesh:
- *Color.*—Yellowish orange (4-A-8) to golden yellow (5-A-7).
- *Juice.*—Abundant, rich.
- *Texture.*—Firm.
- *Fibers.*—Few; Tender.
- *Ripens.*—Comparatively even, but earliest at the apex.
- *Flavor.*—Mild; Distinct resemblance to the Elberta peach.
- *Aroma.*—Pronounced.
- *Eating quality.*—Good to excellent.

Skin:
- *Thickness.*—Medium.
- *Texture.*—Medium; Tenacious to flesh.
- *Down.*—Moderate to heavy.
- *Color.*—Bright yellow ground color (5-A-8) to (4-A-8), nearly completely overspread with light red (8-A-8) to (8-B-8).

Stone:
- *Type.*—Clingstone.

*Fibers.*—Short.
*Size.*—Medium to large; Average length — 1⅝"; Average width — 1 1/16"; Average thickness — ⅝".
*Form.*—Oblong.
*Base.*—Oblique.
*Hilum.*—Oval; Shallow.
*Apex.*—Acuminate.
*Sides.*—Substantially symmetrical.
*Surface.*—Regularly furrowed toward apex.
*Tendency to split.*—Slight.
*Color.*—Light tan.

Uses: Culinary; Dessert; Market, local and long distance shipping.

Keeping quality: Good.
Shipping quality: Good.

The peach tree and its fruit described may vary in slight detail due to climatic conditions under which the variety may be grown; the present description being of the variety as grown in the Central Valley of California.

I claim:

1. A new and distinct variety of peach tree bearing large, yellow flesh, clingstone peaches with a high degree of exterior red color, characterized as to novelty when compared to its seed parent, Royal Gold, (U.S. Plant Pat. No. 2,663) by having fruit of larger size, a higher degree of red color and a greater distribution of uniform fruit throughout the tree.

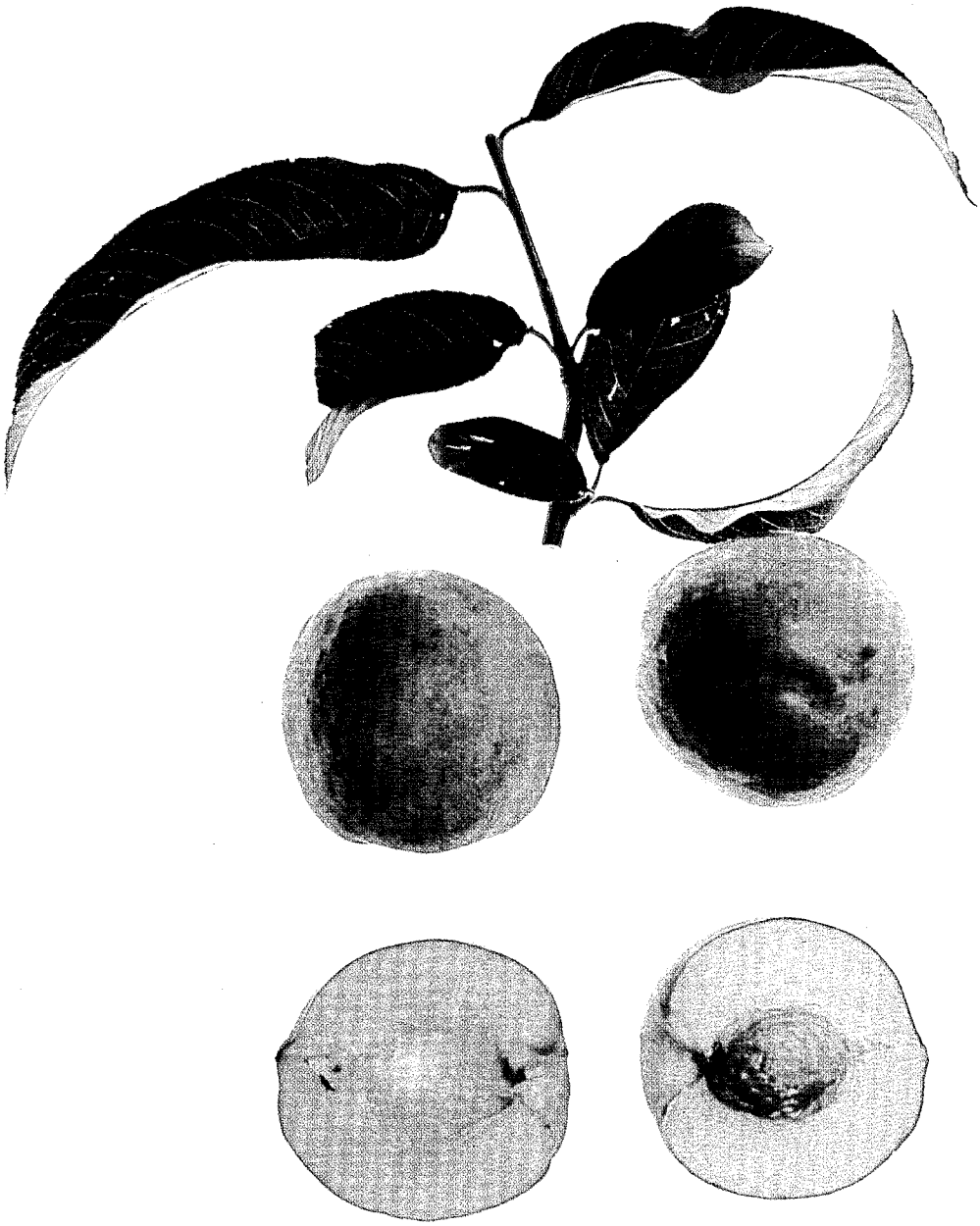

* * * * *